(12) United States Patent
Buendia

(10) Patent No.: US 7,781,407 B2
(45) Date of Patent: *Aug. 24, 2010

(54) CALCIUM GLUCONOLACTATE COMPOSITIONS AND METHODS OF MAKING SAME

(76) Inventor: Manuel Torres Buendia, Calle 9 Este No. 24, Col. Ciup MTL, Jiutepec, Morelos (MX) 62500

( * ) Notice: Subject to any disclaimer, the term of this patent is extended or adjusted under 35 U.S.C. 154(b) by 246 days.

This patent is subject to a terminal disclaimer.

(21) Appl. No.: 11/728,728

(22) Filed: Mar. 26, 2007

(65) Prior Publication Data

US 2008/0026080 A1  Jan. 31, 2008

Related U.S. Application Data

(63) Continuation of application No. 10/874,695, filed on Jun. 23, 2004, now Pat. No. 7,196,179, which is a continuation of application No. PCT/MX02/00058, filed on Jun. 27, 2002.

(51) Int. Cl.
 *A61K 31/70* (2006.01)
 *C07H 1/00* (2006.01)
(52) U.S. Cl. ........................................ 514/23; 536/1.11
(58) Field of Classification Search ........................ None
 See application file for complete search history.

(56) References Cited

U.S. PATENT DOCUMENTS

| 2,813,892 A | 11/1957 | Mehltretter |
| 4,867,977 A * | 9/1989 | Gailly et al. ................. 424/687 |
| 2003/0049284 A1 | 3/2003 | Boccio et al. |

FOREIGN PATENT DOCUMENTS

| EP | 885568 | 12/1998 |
| ES | 8609192 | 12/1986 |
| FR | 2601249 | 1/1988 |

OTHER PUBLICATIONS

John McMurray, Chemistry, 1995, Prentice-Hall. pp. 376-378.

* cited by examiner

*Primary Examiner*—Elli Peselev
(74) *Attorney, Agent, or Firm*—Thorpe North & Western LLP

(57) ABSTRACT

A method to manufacture calcium gluconolactate as a single molecule, compositions formed thereby, and uses therefor are disclosed and described. In one embodiment, a method of manufacturing calcium gluconolactate by reacting a gluconic acid reaction or an equivalent thereof, such as glucono delta lactone with lactic acid in the presence of calcium hydroxide and water to obtain a calcium gluconolactate molecule having the formula $CH_2OH—(CHOH)_4—COOCaCOO—CH(OH)—CH_3$ with molecular weight of 324.2994 is presented.

24 Claims, No Drawings

CALCIUM GLUCONOLACTATE COMPOSITIONS AND METHODS OF MAKING SAME

PRIORITY DATA

This application is a continuation of U.S. patent application Ser. No. 10/874,695, filed Jun. 23, 2004, now U.S. Pat. No. 7,196,179, issued on Mar. 27, 2007, which is a continuation of Patent Cooperation Treaty Application Serial No. PCT/MX02/00058, filed Jun. 27, 2002 each of which are incorporated herein by reference.

THE FIELD OF THE INVENTION

The present invention is related to methods for manufacturing calcium gluconolactate and the compositions formed by these (sic), their processes and their use of it. In particular, the invention is related to methods for manufacturing calcium gluconolactate by means of a gluconic acid reaction or hydrolysis of glucono delta lactone in water with lactic acid in the presence of calcium hydroxide to obtain calcium gluconolactate in a single molecule.

BACKGROUND OF THE INVENTION

There are known procedures to obtain compositions of mixed calcium gluconolactate salt formed by the addition of glucono delta lactone and calcium lactate in the presence of calcium carbonate, as shown in Spanish patent application (ES) No. 544,925. Obtaining the mixed salt of calcium gluconolactate by means of this process does not yield a product with a balanced stiochiometry. For example, at times calcium concentrations below 90% are obtained with the mixed salt, which must then be adjusted to raise the calcium content to acceptable levels. Alternatively, the mixtures obtained with the mixed salt contains an amount of calcium exceeding the maximum acceptable content of 102%, sometimes up to 108%, which is outside the acceptable range and conditions of the reaction. Thus, the reactants fail to produce a compound with a definite molecular weight.

DESCRIPTION OF THE INVENTION

The present invention is related to methods for manufacture (synthesis) of calcium gluconolactate, compositions and molecules formed thereby, and uses therefore. In particular, the invention is related to methods for manufacturing calcium gluconolactate using a gluconic acid reaction or hydrolysis of glucono delta lactone in water with lactic acid in the presence of calcium hydroxide to obtain calcium gluconolactate.

In one aspect, calcium gluconolactate is obtained from the reaction of lactic and gluconic acids in an aqueous medium in the presence of calcium hydroxide, the end product obtained is adjusted to a pH of 4.0 to 5.5 with one of the reactants used, on a case by case basis, and is treated with activated carbon, filtered, and evaporated at low pressure (10 to 25 inches of mercury (in/hg)) to a concentration of 60% to 95% preferably to a concentration of at least 90% to 95%. Finally, the product is dried in a tray drier at approximately 80° C. to 120° C., preferably at an approximate temperature of 95° C. to 115° C., until it reaches a minimum concentration of approximately 95% to 99%, preferably 98%, calcium content in the molecule.

The product obtained in this reaction has a balanced stoichiometry, producing a single molecule of a general formula III, $(CH_2OH—(CHOH)_4—COOCaCOO—CH(OH)—CH_3$, as specified below, with molecular weight (MW) of 324.2994 g/mol, which has not been obtained to date, in other words a compound, or molecule rather than a mixture of calcium lactate and calcium gluconate.

The molecular calcium content obtained with this product is 12.3589%, which corresponds to the theoretical 100%; in other words, with this invention we obtain from a minimum of 98% to 99.9%, preferably 99.5%, of calcium, in accordance with the following formula:

$$\text{theoretical calcium \%} + (40.08/324.2994) \times 100 + 12.3589\%$$

Where

MW of calcium gluconolactate=324.2994 g/mol

MW of calcium=40.08 g/mol

Surprisingly, we can observe that this compound has an advantage over the mixture described above, in that the concentrations obtained with the mixture are below 90% or over 100%, and are adjusted by adding calcium, to achieve acceptable levels. There are mixtures that exceed the maximum acceptable calcium content of 100%, reaching levels as high as 108%, which are outside the acceptable range. In this reaction we are proposing that the calcium content in the compound is maintained in a stiochiometric proportion, giving us a calcium content of approximately 98% to 99.9%, preferably 99.5%, for practical purposes, without the need to add or remove calcium from other sources.

Moreover, the salt obtained is an anhydrous product with a crystalline and non-amorphous appearance, which gives the compound a high degree of solubility. Also, the crystalline obtained is more soluble, as compared with the amorphous form which is less soluble and lacks the physiochemical properties. The crystalline is obtained by applying the temperature and pressure conditions specified in the present invention.

The reaction scheme used to obtain calcium gluconolactate is as follows:

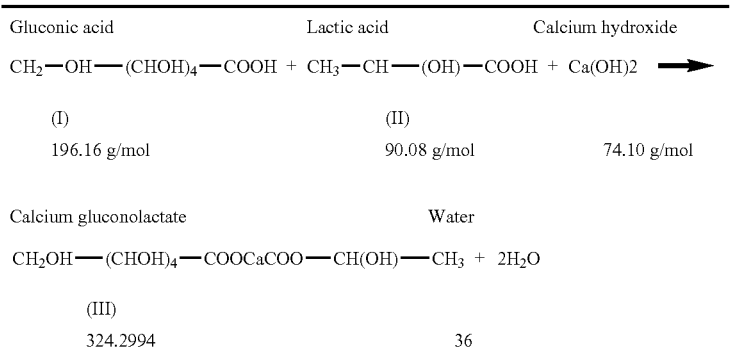

*The reaction yield of calcium gluconolactate corresponds to its stiochiometric [yield].

The compound obtained from formula III has the following physiochemical properties.

1.—Thermal performance of calcium gluconolactate at different temperatures. Because the product does not melt, the performance of calcium gluconolactate on heating is demonstrated by means of the following tests: 1) closed capillary tube; the test is performed in a closed capillary tube, while repeating the procedure 5 times. The initial white to slightly yellowish color (characteristic of the substance) changes to light beige at 158° C., then to beige at 170° C., then changes to golden beige with the product moving toward the top of the tube, continuing until it reaches 204° C., where we observe a toasted brown color with clear signs of decomposition. The average value for the temperature at which the product starts to move is 171° C., ending with decomposition and carbonization at between 204° C. and 213° C.; 2) with Differential Scanning Calorimetry (DSC), we observe a considerable difference in performance between the curve obtained on heating with a cap and orifice, from a curve obtained in a sealed capsule. We clearly observe with, the curve obtained in a sealed capsule, a transition from the fusion step with decomposition at 213° C., which does not mean that the substance melts, and a transition from the vitreous step at 116° C.; 3) with Derivative Thermogravimetry (DTG), we observe the start of decomposition (weight loss) at approximately 170° C., and at the end of the sample it is observed to be totally inflated and carbonized at between 204° C. and 213° C., in DTG, which is the derivative of the TG (thermogravitmetry) curve. Furthermore, we clearly observe peak decomposition at between 170° C. and 250° C.; 4) with Differential Thermal Analysis (DTA), we observe the start of decomposition (weight loss) at approximately 170° C., and at the end, the sample was observed to be totally inflated and carbonized at between 204° C. and 213° C.; DTA corroborates the peak decomposition temperature of between 170° C. and 250° C., with considerable fading due to the sample's contact with the thermopair. The results are shown in table I below:

TABLE I

THERMAL PERFORMANCE OF CALCIUM GLUCONOLACTATE TEMPERATURES

| Test No. 1 ° C. | Test No. 2 ° C. | Test No. 3 ° C. | Test No. 4 ° C. | Test No. 5 ° C. | Observations |
|---|---|---|---|---|---|
| 156 | 157 | 158 | 158 | 158 | Light beige |
| 169 | 171 | 170 | 170 | 170 | Beige |
| 169 | 168 | 174 | 173 | 172 | Starts to move toward the top of the capillary tube golden brown |
| 203-213 | 205-213 | 204-213 | 204-213 | 204-213 | Toasted brown, maintaining the same movement and starting to decompose with carbonization |

The average value for the temperature at which the product starts to move is 171° C.

In the (DSC) method, a Mettler Toledo model 821 differential scanning calorimeter and a Mettler Toledo model 851 thermobalance were used.

Method used: from 0 to 350° C., with heating speed of 10° C./min. in and inert nitrogen atmosphere at 10 ml/min.

Results and observations: In DSC a sample was run in a capsule with lid and orifice, [and] another sample in a sealed capsule. A considerable difference in performance between the curve obtained on heating with a cap with orifice and the curve obtained in a sealed capsule, where we could clearly observe a transition from the fusion step with decomposition (213° C.), which does not mean that the substance melts, and a transition from the vitreous step (116° C.).

In TG/DTG/DTA we observe the start of decomposition (weight loss) at approximately 170° C. On finalizing the test the sample was observed to be totally inflated and carbonized at between 204° C. and 213° C.

In DTG, which is the derivative of the TG curve, we clearly observe peak decomposition at between 170° C. and 250° C.

In DTA the peak decomposition is corroborated, the sample was observed to be considerably faded due to its contact with the thermopair, as a result of DSC's higher resolution.

As the methods described above, in order to confirm that the product does not have a specific fusion point, the experimentally defined thermal performance must show, a change in color as indicated in table 1 until it reaches decomposition and carbonization.

2.—Apparent and compacted bulk density; for the test calcium gluconolactonate, from formula III, was classified in 3 different types of mesh 30, 80, and 100 to determine its apparent density. The same procedure was used to determine compacted bulk density. The compound was classified in the same 30, 80, and 100 meshes, determining its density, in both cases, in grams per milliliter, as shown in table II below:

TABLE II

| Test | Result | Method |
|---|---|---|
| Apparent Density (30 mesh) | 0.690 g/ml | Mass/Volume |
| Apparent Density (80 mesh) | 0.655 g/ml | Mass/Volume |
| Apparent Density (100 mesh) | 0.609 g/ml | Mass/Volume |
| Compacted Bulk Density (30 mesh) | 0.883 g/ml | Mass/Volume |
| Compacted Bulk Density (80 mesh) | 0.904 g/ml | Mass/Volume |
| Compacted Bulk Density (100 mesh) | 0.874 g/ml | Mass/Volume |

The average density corresponds to a 30 mesh, for the most common form of the product. A table is attached with different tests performed to determine the average apparent and compacted bulk density, resulting, in the first case, in a[n apparent] density of 0.690 and a compacted bulk density of 0.883, as shown in table III below:

TABLE III

DENSITIES (30 MESH)

| Test | Apparent | Compacted Bulk |
|---|---|---|
| 1 | 0.718 | 0.898 |
| 2 | 0.706 | 0.905 |
| 3 | 0.703 | 0.901 |
| 4 | 0.742 | 0.927 |
| 5 | 0.715 | 0.917 |
| 6 | 0.691 | 0.886 |
| 7 | 0.671 | 0.883 |
| 8 | 0.662 | 0.868 |
| 9 | 0.681 | 0.897 |
| 10 | 0.681 | 0.896 |
| 11 | 0.695 | 0.892 |
| 12 | 0.681 | 0.873 |
| 13 | 0.663 | 0.851 |
| 14 | 0.652 | 0.859 |
| 15 | 0.671 | 0.86 |
| 16 | 0.643 | 0.858 |
| 17 | 0.665 | 0.887 |
| 18 | 0.708 | 0.983 |
| 19 | 0.701 | 0.899 |
| 20 | 0.686 | 0.887 |
| 21 | 0.658 | 0.866 |
| 22 | 0.707 | 0.895 |
| 23 | 0.687 | 0.881 |
| 24 | 0.695 | 0.879 |
| 25 | 0.713 | 0.892 |
| 26 | 0.701 | 0.834 |
| 27 | 0.706 | 0.821 |
| 28 | 0.727 | 0.846 |
| 29 | 0.657 | 0.864 |
| 30 | 0.706 | 0.883 |
| 31 | 0.711 | 0.911 |
| average | 0.690 | 0.883 |

3.—Solubility; the compound is slowly soluble in one part water at 25° C. with saturation and easily soluble in 5 parts. The compound is easily soluble in two parts of boiling water, and slowly soluble in one part with saturation, and practically insoluble in methanol and in alcohol. Values are shown in table IV below (the table shows the degree of solubility in different proportions of water).

4.—pH: The 5% solution calcium gluconolactate characteristically presents a pH of between 5.5 and 6.5.

TABLE IV

| Weight-volume ratio | Solubility in water at 25° C. | Solubility in boiling water |
|---|---|---|
| 1:5 | Easily soluble | Easily soluble |
| 1:4 | Soluble | Easily soluble |
| 1:3 | Soluble | Easily soluble |
| 1:2 | Slowly soluble | Easily soluble |
| 1:1 | Slowly soluble and becomes Saturated | Soluble and becomes saturated |

5.—Physical appearance: calcium gluconolactate characteristically has the appearance of a slightly yellowish crystalline powder or irregularly shaped, white to slightly yellowish crystals, with a mild odor which is a characteristic of the product.

6.—Low- and high-resolution mass spectrometry (MS), where various tests were performed to experimentally determine molecular weight, which is 324.2994, and high resolution elemental analysis giving a composition $C_9H_{16}O_{10}Ca$ corresponding to the calcium gluconolactate molecule.

Sample Preparation:

The sample was analyzed in Jeol model SX-102A (dual sector, inverse geometry) Mass Spectrometer. Due to the nature of the sample (Calcium Gluconolactate), the Fast Atom Bombardment (FAB) ionization technique with negative ion detection was used.

Analysis conditions for Low Resolution were as shown in Table V below:

TABLE V

| | |
|---|---|
| Sample identification: | Sample -2 |
| Sample preparation: | The solid was ground and the matrix and water were added. |
| Sample introduction: | Direct introduction |
| Ionization method: | Fast atom bombardment (FAB) |
| Ion detection: | Negative |
| Gas for bombardment | High purity xenon |
| Matrix used | Glycerol |
| Mass range (SCAN mode) | 10-2000 um |
| Calibration standard | Ultramark 1621 (perfluoroalkylphosphine) |
| Ionization chamber temperature: | 25° C. |
| Resolution: | 3,000 (low resolution) |
| Scan Type | Magnetic field |

Information: Chemical structure of the experimental sample

Calcium Gluconolactate:

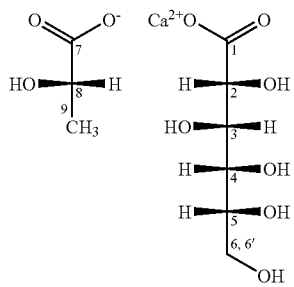

Condensed formula: $C_9H_{16}O_{10}Ca$

Molecular weight: 324 um (unit of mass)

Chemical Structure of the Matrix

Glycerol:

$CH_2$—OH

CH—OH
CH$_2$—OH
Condensed formula: C$_3$H$_8$O$_3$
Molecular weight: 92

High-resolution mass spectrometry analysis; the sample was analyzed in a Jeol model SX-102A (dual sector, inverse geometry) mass spectrometer. Due to the nature of the sample (Calcium gluconolactate) the Fast Atom Bombardment (FAB) ionization technique with negative ion detection was used.

Analysis conditions for High Resolution were as shown in Table VI below:

TABLE VI

| | |
|---|---|
| Sample identification: | Sample -2 |
| Sample preparation: | The solid was ground and the matrix and water were added. |
| Sample introduction: | Direct introduction |
| Ionization method: | Fast atom bombardment (FAB) |
| Ion detection | Negative |
| Gas for bombardment | High purity xenon |
| Matrix used | Polyethyleneglycol |
| Mass range (SCAN mode) | 50-350 uma |
| Calibration standard | Polyethyleneglycol (PEG 200) |
| Ionization chamber temperature: | 25° C. |
| Resolution: | 5,000 (high resolution) |

Analysis of Results:

| Compound | Theoretical Monoisotopic Molecular Weight | Experimentally Obtained Monoisotopic Molecular Weight | Difference in mmu | Error (pMW) | Elemental Composition |
|---|---|---|---|---|---|
| Lactate ion | 89.0239 | 89.0247 | +0.8 | 3.9 | C$_3$H$_5$O$_3$ |
| Gluconate ion | 195.0605 | 195.0512 | +.08 | 8.9 | C$_6$H$_{11}$O$_7$ |

\* of tolerance: +/−10 mmu (mass mili-units)
ERROR (pMW) = Difference in mmu (between real and theoretical monoisotopic mass) × 10$^6$ Theoretical monoisotopic mass.

Analysis of Results

Mass Spectrum Interpretation by FAB with Glycerol Matrix

| Mass | Composition |
|---|---|
| Masses of glycerol ions with significant Abundance due to negative FAB | |
| 91 | (C$_3$H$_7$O$_3$) |
| 183 | (C$_6$H$_{15}$O$_6$) |
| 275 | (C$_9$H$_{23}$O$_9$) |
| 367 | (C$_{12}$H$_{31}$O$_{12}$) |
| 459 | (C$_{15}$H$_{39}$O$_{15}$) |
| 551 | (C$_{18}$H$_{47}$O$_{18}$) |
| 643 | (C$_{21}$H$_{55}$O$_{21}$) |
| 735 | (C$_{24}$H$_{63}$O$_{24}$) |
| Ion masses due to negative FAB of calcium gluconolactate (Sample -2) in glycerol matrix | |
| 89 | (C$_3$H$_5$O$_3$) -approximate intensity 50%)Lactate ion |
| 195 | (C$_6$H$_{11}$O$_7$) -approximate intensity 25%) Gluconate ion |
| 323 | (C$_9$H$_{15}$O$_{10}$Ca) - approximate intensity 14%) (M-H) - Ion |

Finally, as the intensity/mass over load figures show, signs can be observed of the lactate ion with mass of 89, and the gluconate ion with mass of 195 and calcium gluconolactate with mass of 323 corresponding to that of the molecule minus a proton [M−H$^+$]—resulting from the loss of one of the protons in the polyhydroxilate group forming the system.

Conclusions:

The m/x=323 (M−H) ion observed in the low-resolution negative FAB spectrum does not appear in the high resolution spectrum, possibly because the field scan used to obtain the masses must be different for low resolution (magnetic field) than for high resolution (electric field). Also, the matrix used was polyethyleneglycol, being of calibration standard, which modifies ion desorption and the abundance of ions in the spectrum.

On the other hand, as resolution is increased, sensitivity is invariably lost and some less abundant ions, that appear in a low-resolution mass spectrum, consequently are "lost" (fail to reach the detector) in high-resolution analysis.

With the results obtained, we can conclude, based on the low-resolution mass spectrum, that the sample contains the ions: lactate, gluconate, and calcium gluconolactate. High-resolution mass spectrometry can only confirm the lactate and gluconate ions.

7.—Identification by nuclear magnetic resonance; a calcium gluconolactate sample was subject to $^1$H analysis, and the sample was prepared by dissolution in D$_2$O and was taken as reference for the internal $^1$H spectrum of HDO at 4.67 pMW. The $^1$H spectrum results are shown in Table VII below:

TABLE VII

| Sign No. | Chemical Displacement INSERT SYMBOL pMW | Integral | $^1$H Type |
|---|---|---|---|
| 1 | 1.192 | 3 | CH$_{3\,(9)}$ |
| 2 | 3.511 | 1 | H de CH$_{2\,(6\,O\,6')}$ |
| 3 | 3.626 | 1 | CH$_{(4)}$ |
| 4 | 3.641 | 1 | H de CH$_{2\,(6\,O\,6')}$ |
| 5 | 3.676 | 1 | CH$_{(5)}$ |
| 6 | 3.952 | 1 | CH$_{(3)}$ |
| 7 | 4.026 | 1 | CH$_{(8)}$ |
| 8 | 4.086 | 1 | CH$_{(2)}$ |

Condensed formula: C$_9$H$_{16}$O$_{10}$Ca
Calcium Gluconolactate:

8.—Identification by infrared (IR) spectrometry; various tests were performed to identify the compound. An infrared spectrogram was performed using the Potassium Bromide tablet and Nujol methods; the spectrogram identified the following functional groups:

a) O—H in the sample; an intense, wide stripe was identified in the region of 3200-3600 cm$^{-1}$, which is due to the lengthening of the O—H, for O—Hs in the pentahydroxyls of caproic acid, of the hydroxyl of propanoic acid, and of the water molecules that may be retained in the sample, as well as an intense wide stripe, due to the lengthening of the C—O in the 1000-1200 cm$^{-1}$ region, of the same alcoholic nature as the aforementioned acids.

b) Methyl and methylene; An intense stripe was identified in the 2850-2960 cm$^{-1}$ region corresponding to the lengthening of the C—H of a hydrocarbon, along with other stripes in the 1300-1460 cm$^{-1}$ range, characteristic of the terminal methyl —CH$_3$ group and the methlyene —CH$_2$ [group] in the 1460 cm$^{-1}$ region of the stripe.

c) C═O; An intense, wide stripe was identified in the 1590-1610 cm$^{-1}$ region due to the lengthening of the C═O characteristic of a carbonyl and the stripes showing lengthening of C—O in the region of the 1050-1200 cm$^{-1}$ stripe characteristic of carboxyl groups, these stripes depend on the bonds that these acids contain, as confirmed by the infrared spectrum of calcium lactate, shown below.

Calcium Lactate
CAS Registration No.: 5743-47-5
Chemical Structure:

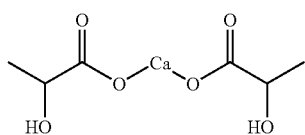

The presence of the functional groups in the sample analyzed and those confirmed by the characteristic stripes of the aforementioned salt, confirm comparatively, that the structure of the molecule corresponds to calcium gluconolactate, given that no other functional group were observed aside from those indicated above.

9.—Based on the molecular weight determined by mass spectrometry, the corresponding miliequivalent was used to determine ionizable calcium content and the following analytical procedure was used to determine calcium content.

Evaluation; Weigh 0.5 grams of synthetic calcium gluconolactate, dissolve in 150 ml of water and 2 ml of 3 N chlorhydric acid solution, agitate with a magnetic agitator. With a burette add 20 ml of a 0.05M solution of disodium edetate, add 15 ml of a 1 N sodium hydroxide solution and add 300 mg of hydroxynaphtol blue indicator and continue titration to blue end point.

Each ml of 0.05M disodium edetate solution is equivalent to 16.21497 mg of calcium gluconolactate Calculations:

% Content=ml of EDTA 0.05 M×EDTA factor×meq× 100/weight of sample

Where:
meq: Miliequivalent of calcium gluconolactate=0.01621497 grams.

10.—Liquids chromatography, using High-Pressure Liquids Chromatography (HPLC).

Measurement of gluconic acid and lactic acid by high-pressure liquids chromatography, and of calcium by spectroscopy of emissions contained in calcium gluconolactate samples.

Evaluation of gluconic acid and lactic acid by liquids chromatography.

Reactants
Reference Pattern for calcium gluconolactate
Potassium phosphate monobasic
Phosphoric acid at 68%
Chromatography grade water
Standard secondary lactic acid
Standard secondary gluconic acid Conditions of Equipment

TABLE NO. 1

| CALIBRATION CURVE | | | | |
|---|---|---|---|---|
| Mobile phase: | 20 mM of potassium phosphate pH 2.8 | | | |
| Detector: | ultraviolet | | | |
| Wavelength: | 215 nm | | | |
| Column: | Aqua C18, 5 micros, 250 mm × 4.6 mm. | | | |
| Flow: | 1.5 ml/minute | | | |
| QUANTITY ug/ml | AREA | QUANTITY ug/ml | AREA | |
| A    361.88 | 138180 | 187.27 | 103985 | |
| B    482.51 | 182224 | 268.42 | 148751 | |
| C    603.13 | 230166 | 349.57 | 193884 | |
| D    723.76 | 280530 | 436.96 | 243701 | |
| LEVEL | GLUCONIC ACID | | LACTIC ACID | |
| Injection vol.: | 20 microliters | | | |

The calibration curve was plotted with the reference pattern for calcium gluconolactate at 4 concentration levels, as indicated below

| Sample weight | % | Sample weight | % | Sample weight | % | % Total |
|---|---|---|---|---|---|---|
| 1   106.89 | 27.06 | 106.89 | 58.05 | 22.45 | 13.22 | 98.33 |

According to the calibration curves, the following percentages were obtained from the samples analyzed, the calcium content was measured by emissions spectroscopy.

Composition in Percentage of Calcium Gluconolactate Components in the Sample.

| MS | LACTIC ACID | GLUCONIC ADIC | CALCIUM |
|---|---|---|---|

CONCLUSIONS

As can be observed in Table No. 2, the sample contains lactic acid percentage of 27.06%, near the theoretical quantity for lactic acid (27.468%).

For gluconic acid, we also find a percentage of 58.05 [%], near the theoretical quantity for gluconic acid (60.178%).

As regards to calcium, we find an average value of 12.2% to 13.22%, which, in accordance with the theoretical value of 12.36% for calcium, corresponds to the molecular content, as determined by inductively coupled plasma emissions spectroscopy. Atomic emissions spectroscopy is a process in which the light emitted excites the atoms or ions measured, emissions occurs when there is sufficient thermal energy in argon plasma, which excites the free atoms or ion in an unstable energetic state. Light is emitted when the atom or ion returns to a more stable configuration. The light wavelengths emitted are specific to the elements present in the sample. The light emitted is measured by segments in the instrument and compared with a known emitted light as a reference standard.

| | |
|---|---|
| Instrument | PerkinElmer P2000, Optima 3000 or equivalent |
| Decomposition | Selection of appropriate solubilization or digestion method. |
| Calibration | Standard sample |
| Introduction of the sample | The sample in solution is nebulized, the resulting aerosol is transported to the plasma torch (15 L/min; 1400 watts). |
| Measurement | Primary wavelength at 393.4 nm; direct reading |
| Detection limit | Varies with the matrix of the individual sample, but is appropriate for solutions below the equivalent antecedent of 0.01 mg/L concentration. |
| Precision and accuracy (I.2202) | |
| RSD | 2.68% |
| RE | −1.10% |
| Interference | Spectral only |
| Calculations | The microprocessor provides the final ug/ml concentration |

$$PMW = \frac{(\text{Final concentration} \times V \times D)}{\text{grams of the sample}}$$

$$\% = \frac{(\text{Final concentration} X V \times D)}{10 \text{ mg of the sample}}$$

V = Volume of the sample in ml; D = Dilution factor

With this data we observe that the sample has a balanced stoichiometry as compared with the theoretical calcium gluconolactate molecule.

These values are determined by high-resolution liquid chromatography. The lactic and gluconic ions correspond to the stiochiometric ratio of the content, and the values for calcium in the proportions found by emissions spectrometry also correspond to the stoichiometry of the compound obtained from formula III. The values may vary slightly depending on calcium content and may be from 98% to 99.9%, preferably 99.5%.

The stiochiometric ratio, in percentage by weight of raw materials is as follows:

| | |
|---|---|
| Lactic acid | 10% to 30% |
| Calcium hydroxide | 7% to 25% |
| Gluconic acid | 40% to 65% |
| Water as vehicle in percentage by weight of raw materials | 10% to 70% |

* activated carbon

Preferably, the stiochiometric ratio, in percentage by weight of raw materials is as follows:

| | |
|---|---|
| Lactic acid | 27.47% |
| Calcium as Calcium hydroxide | 12.36% |
| Gluconic acid | 60.17% |
| Water as vehicle in percentage by weight of raw materials | 61% |

* activated carbon

Methods of manufacture (synthesis) of calcium gluconolactate by gluconic acid reaction or glucono delta lactone hydrolysis in water with lactic acid in the presence of calcium hydroxide to obtain calcium gluconolactate in a single molecule are described below.

the method of manufacture (synthesis) comprises the following steps:

1) load filtered water, at approximately 10% to 70%, preferably 61% in a reactor equipped with an agitator and heating sleeve; 2) Agitate and add calcium hydroxide at approximately 7% to 25%, preferably 22.85%; 3) Continue to agitate long enough to homogenized; 4) while agitating, gradually add lactic acid at approximately 10% to 30%, preferably 27.47% and heat to approximately 70° C. to 110° C.; 5) maintain temperature in a range of approximately 70° C. to 110° C. long enough for the reaction to stabilize; 6) cool mixture to approximately 70° C. to 90° C.; 7) constantly adding gluconic acid or its equivalent, glucono delta lactone, at approximately 40% to 65%, preferably 60.17%. Continue to agitate the reactor and maintain the reaction temperature at approximately 70° C. to 90° C. for approximately 6 hours, from the start of the reaction until the reaction ends; 8) when the reaction has ended, adjust pH to between 4.0 and 5.5, with any of the appropriate reactants and add activated carbon in sufficient quantity to decolorize the solution; 9) filter the solution to eliminate materials in suspension; 10) use low-pressure drying to evaporate the filtered solution in an evaporator equipped with an agitator and heating sleeve at low pressure of approximately 10 to 25 inches of mercury (in/Hg), in a temperature range of approximately 50° C. to 120° C., preferably 68° C. to 72° C. Achieving a concentration of approximately 60% to 95%, preferably 90% to 95%, so that the product crystallizes in its crystalline form and not its amorphous form; 11) the end product obtained by a final drying step in a tray drier at approximately 80° C. to 120° C. long enough to reach a minimum concentration of approximately 95% to 99%, preferably 98.0%.

This method of manufacture or synthesis makes it possible to obtain stiochiometric molar quantities of a single calcium gluconolactate molecule, with a definite molecular weight. In accordance with its stoichiometry, we may obtain a product by means of a chemical reaction which takes place at low-pressure conditions, crystallization of a product without solvents, and at low pressure and drying of the product at a high temperature.

The product obtained by this method of synthesis allows us to achieve a product with a balanced stoichiometry, yielding a single molecule with MW of 324.2994, which had not been identified previously.

The calcium gluconolactate obtained can be used alone or in combination with excipients, known to persons with specialized technical knowledge in the field, to form or prepare pharmaceutical or nutritional compositions or medications.

The calcium gluconolactate obtained can be used as a general calcifying agent, to prevent hypocalcaemia, hyperparathyroidism, osteomalacia, rickets, and symptomatic treatment of osteoporosis, especially in menopause. The calcifying agent may be used to calcify in breast feeding and to calcify in children. In the different stages of human development or in case of specific complaints, increased calcium intake is needed to avoid serious complications, such as hypocalcaemia and osteoporosis caused, basically, by the stages of growth, breast feeding and menopause, among others. Studies have shown that the use of calcium gluconolactate in combination with calcium carbonate, in recommended doses varying between 0.5 grams and 1 gram of calcium per day, help prevent the aforementioned clinical conditions.

These studies have been conducted with patients and research subjects of all ages, as the studies performed show.

The preferred presentation is in the form of effervescent calcium mixed with excipients such as a citric acid, bicarbonate of soda to make it effervescent and soluble, etc. For example, effervescent tablets with any kind of excipients such as citric acid, bicarbonate of soda, saccharine, aspartame, pluracol, sodium benzoate sodium, glycerin, lactose, ethyl alcohol, isopropyl alcohol, and water-soluble flavorings.

A pharmaceutical compositions includes a calcium gluconolactate compound in combinations with calcium carbonate and one or more pharmaceutically acceptable vehicles known in the trade.

A pharmaceutical composition that contains calcium gluconolactate and is mixed with glycerin or sodium benzoate and alcohol to give it an agglomerating property that enables it to agglutinate other vehicles or excipients, including calcium carbonate, as the active ingredient allowing us to obtain an effervescent tablet.

EXAMPLES

Example 1

Load 900 liters of filtered water in a reactor fitted with an agitator and heating sleeve, agitate and then add 135.28 Kg of calcium hydroxide. Continue to agitate long enough to homogenize the reaction mixture. While agitating gradually add 177.53 Kg of lactic acid and heat to approximately 70° C. to 110° C., preferably 98° C., maintaining temperature in a range of approximately 70° C. to 110° C., long enough for the reaction to stabilize. Then cool to approximately 70° C. to 90° C. Continue by adding 312.12 Kg of glucono delta lactone, while continuing to agitate the reactor and maintaining the reaction temperature of approximately 70° C. to 110° C. for 6 hours from the start until the reaction ends. Once the reaction has stopped, adjust pH to between 4.0 and 5.5 with any of the aforementioned reactant, as the case may be. Then add 2.0 Kg of activated carbon to decolorize the solution. After being treated with activated carbon the solution is filtered to eliminate materials in suspension. The filtered solution is then exposed to low pressure drying, the solution is filtered in an evaporator, fitted with an agitator and heating sleeve at low pressure of between 10 and 25 inches/mercury (in/Hg), in a temperature range of approximately 50° C. to 120° C., preferably 68° C. to 72° C. The solution is dried until it reaches an approximate concentration of 60% to 95%, preferably 90% to 95%. The end product obtained by a final drying step, in a tray drier at an approximate temperature of 80° C. to 120° C., preferably 110° C. for long enough to reach a minimum concentration of approximately 95% to 99%, preferably 98.0%.

Example 2

The same conditions described in Example 1 were used, with the exception of 6 moles of lactic acid are made to react with 4 moles of gluconic acid or the equivalent in glucono delta lactone. Also, 5 moles of calcium hydroxide or calcium carbonate in an aqueous medium, is used to obtain 3 moles of calcium lactate, 2 moles of calcium gluconate, and water.

Example 3

The same conditions described in Example 1 were used with the exception of reacting 3 parts of calcium lactate with 2 parts of calcium hydroxide or calcium carbonate in an aqueous medium, to obtain a calcium gluconolactate mixture in a proportion of 3/2.

Example 4

The same conditions described in Example 1 were used, however, instead of using gluconic acid, glucono delta lactone was used in an equivalent amount to form the same quantity of gluconic acid required in Example 1 and with a total of 900 liters of reaction water.

Example 5

The same conditions as described in Example 2 are used, with the exception of low pressure evaporation is used to achieve a concentration of approximately 50% to 80%, preferably 62%. Also, precipitating the mixture with methyl alcohol, ethyl alcohol or a mixture of the two in a V/V proportion of 3:1 to 6:1, preferably 5:1, and centrifuging mixture to separate the product obtained.

The residual water and alcohol are concentrated to obtain the rest of the product and incorporate it in the first part of the final drying step, as described in Example 1.

Example 6

The same conditions as described in Example 3 are used, with the exception of low-pressure evaporation and obtaining the product by precipitation in line with Example 5.

Example 7

A composition was formulated that has calcium gluconolactate with excipients in the following proportions:

| | |
|---|---|
| Calcium gluconolactate | 40% to 50% |
| Calcium carbonate | 4% to 6% |
| Glycerin | 0% to 5% |
| Citric Acid | 20% to 40% |
| Bicarbonate of Soda | 10% to 25% |
| Pluracol | 0% to 10% |
| Saccharine | 0% to 2% |
| Sodium Benzoate | 0% to 4% |
| Ethyl Alcohol | 0% to 50% |
| Isopropyl Alcohol | 0% to 50% |
| Flavoring | 0% to 2% |
| Lactose | 0% to 10% |

Example 8

The same conditions as described in Example 1 are used, with the exception of equimolar quantities of lactic acid are made to react with equimolar quantities of gluconic acid or glucono delta lactone under the same conditions with equimolar quantities with calcium hydroxide or calcium carbonate in an aqueous medium to obtain an equimolar composition of calcium gluconolactate yielding a product. The product may contain water of crystallization or not, used basically to obtain a compound like that described in Example 1 with a composition that may vary from the stiochiometric [composition], but always maintaining equimolar balance in the reaction, giving us, as the result, knowledge of the composition obtained.

The present invention ought not to be considered limited to the specific examples set forth above, but should be understood to cover all aspects of the invention, as is made clear in the attached claims. Various modifications, equivalent processes, and numerous structures to which the present invention can be applicable and will be easily understandable to experts in the field for which the present invention is intended on revision at the time of the specification.

What is claimed is:

1. A calcium gluconolactate compound having the structure as shown in formula III:

 Formula III produced by the steps of: providing a lactic acid compound, a calcium hydroxide compound, and a glucono compound in solution; reacting the compounds to achieve a reaction mixture; and adjusting the pH of the reaction mixture to a range of about 4.0 to about 5.5.

2. The calcium gluconolactate compound of claim 1, wherein the calcium gluconolactate compound is characterized by apparent and compacted bulk density of 0.690 and 0.883, respectively, classified in 30 mesh.

3. The calcium gluconolactate compound of claim 1, wherein the calcium gluconolactate compound is characterized by its solubility, being slowly soluble in one part water at 25° C. with saturation and easily soluble in 5 parts water, easily soluble in two parts boiling water, and slowly soluble in one part with saturation, and practically insoluble in methanol and in alcohol.

4. The calcium gluconolactate compound of claim 1, wherein the calcium gluconolactate compound is characterized by a pH of 5.5 to 6.5 in a 5% solution.

5. The calcium gluconolactate compound of claim 1, wherein the calcium gluconolactate compound is characterized by a molecular weight of 324.2994 measured experimentally using negative mode, low resolution, Fast Atom Bombardment (FAB), and its elemental analysis determined by the same negative mode, Fast Atom Bombardment (FAB) in high resolution, giving a composition of $C_9H_{16}O_{10}Ca$, corresponding to the calcium gluconolactate molecule, as shown by the values in intensity/mass over load graphs, having the following ionized masses: lactate ion with mass of 89, and gluconate ion with mass of 195, and calcium gluconolactate with mass of 323 corresponding to the mass of the molecule minus one proton [M−H$^+$]—due to the loss of one of the protons in the polyhydroxilate group forming the system.

6. The calcium gluconolactate compound of claim 1, wherein the calcium gluconolactate compound is characterized by having the following, experimentally obtained nuclear magnetic resonance values:

| Sign NO. | Chemical Displacement INSERT ( ) pMW | Integral | $^1$H Type |
|---|---|---|---|
| 1 | 1.192 | 3 | $CH_{3\,(9)}$ |
| 2 | 3.511 | 1 | H de $CH_{2\,(6\,O\,6')}$ |
| 3 | 3.626 | 1 | $CH_{(4)}$ |
| 4 | 3.641 | 1 | H de $CH_{2\,(6\,O\,6')}$ |
| 5 | 3.676 | 1 | $CH_{(5)}$ |
| 6 | 3.952 | 1 | $CH_{(3)}$ |
| 7 | 4.026 | 1 | $CH_{(8)}$ |
| 8 | 4.086 | 1 | $CH_{(2)}$ |

7. The calcium gluconolactate compound of claim 1, wherein the calcium gluconolactate compound is characterized by a value in its calcium gluconolactate miliequivalent equal to 0.01621497 grams, considering that each milliliter of 0.05M disodium edetate solution is equivalent to 16.21497 mg of calcium gluconolactate, the value for calcium determined by plasma emissions spectroscopy.

8. The calcium gluconolactate compound of claim 1, wherein the calcium gluconolactate compound is characterized by the values determined by high-pressure liquids chromatography for lactic and gluconic ions corresponding to the stiochiometric ratio of its content, and the values for calcium in the proportions found by emissions spectrometry also correspond to the stoichiometry of the compound obtained from formula III, where values may vary slightly depending on calcium content and may range from 98% to 99.9%, preferably 99.5%.

9. The calcium gluconolactate compound of claim 1, wherein the calcium gluconolactate compound is characterized by the values determined by infrared spectrophotometry using the Potassium Bromide tablet and Nujol methods, having the following functional groups in the spectrogram: a) O—H in the sample, an intense, broad stripe is identified in the 3200-3600 cm$^{-1}$ region, which is caused by the lengthening of the O—H, for the O—Hs in the pentahydroxyls of caproic acid, the hydroxyl in propanoic acid, and the water molecules that may be retained in the sample, and a wide, intense stripe due to the lengthening of the C—O in the 1000-1200 cm$^{-1}$ region, of the same alcoholic nature as the aforementioned acids; b) Methyl and methylene an intense stripe is identified in the 2850-2960 cm$^{-1}$ region, corresponding to the lengthening of the C—H of a hydrocarbon, along with other stripes in the 1300-1460 cm$^{-1}$ range characteristic of the —CH$_3$ terminal methyl group and the —CH$_2$ methylene group in the 1460 cm$^{-1}$ region of the stripe; and c) C=O, a broad, intense stripe is identified in the 1590-1610 cm$^{-1}$ region due to the lengthening of the C=O characteristic of a carbonyl and by the stripes indicating lengthening of the C—O in the 1050-1200 cm$^{-1}$ region of the stripe characteristic of carboxyl groups.

10. A pharmaceutical composition comprising the calcium gluconolactate compound of claim 1 in combination with calcium carbonate and one or more pharmaceutically acceptable vehicles.

11. The pharmaceutical composition of claim 10, further comprising an excipient wherein the vehicle or excipient is chosen from the following compounds: citric acid, bicarbonate of soda, pluracol, saccharine, lactose, ethyl alcohol, isopropyl alcohol, aspartame, and water-soluble flavorings in combination with sodium benzoate and glycerin.

12. The calcium gluconolactate compound of claim 1, wherein the calcium gluconolactate compound is characterized by the following thermal performance:
   i) in a sealed capillary tube, the initial white to slightly yellowish color (characteristic of the substance) changes to light beige at 158° C.,
   ii) then changes to beige at 170° C.,
   iii) then changes to a golden beige with the product moving to the top of the capillary tube, and continues until it reaches a temperature of 204° C., where a toasted brown color with clear signs of decomposition is observed, and
   iv) where the average value for the temperature at which the product starts to move is 171° C. and ends with decomposition and carbonization at 204° C. to 213° C., wherein the test is performed in a sealed capillary tube repeated 5 times.

13. The calcium gluconolactate compound of claim 1, wherein the calcium gluconolactate compound is characterized by the following thermal performance in Differentional Scanning Calorimetry (DSC):
   i) a difference in performance between the curve obtained on heating with a cover with orifice and the curve obtained in a sealed capsule is observed, where a transition from the fusion type with decomposition at 213° C. is observed, this does not mean that the substance melts, and
   ii) a transition from the vitreous type at 116° C.

14. The calcium gluconolactate compound of claim 1, wherein the calcium gluconolactate compound is characterized by the following thermal performance in Derivative Thermogravimetry (DTG):
  i) the start of decomposition (weight loss) occurs at approximately 170° C.,
  ii) the sample is totally inflated and carbonized at between 204° C. and 213° C., and
  iii) peak decomposition is at between 170° C. and 250° C.

15. The calcium gluconolactate compound of claim 1, wherein the calcium gluconolactate compound is characterized by the following thermal performance in differential Thermal Analysis (DTA):
  i) the start of decomposition (weight loss) at approximately 170 ° C.,
  ii) the sample is totally inflated and carbonized at between 204° C. and 213° C., and
  iii) peak decomposition at between 170° C. and 250° C.

16. The calcium gluconolactate compound of claim 1, wherein the calcium gluconolactate compound is in a crystalline form.

17. The calcium gluconolactate compound of claim 1, further comprising the step of extracting the calcium gluconolactate compound from the reaction mixture.

18. The calcium gluconolactate compound of claim 17, wherein extracting incorporates the steps of filtering and evaporating at low pressures.

19. The calcium gluconolactate compound of claim 18, wherein the low pressure is between 10 to 25 inches of mercury.

20. The calcium gluconolactate compound of claim 1, wherein reacting incorporates the step of adjusting the temperature of the reaction mixture.

21. The calcium gluconolactate compound of claim 20, wherein the temperature is in a range of about 70° C. to about 110° C.

22. The calcium gluconolactate compound of claim 1, wherein the glucono compound is either gluconic acid or glucono delta lactone.

23. The calcium gluconolactate compound of claim 1, wherein the reacting step requires approximately 6 hours for reaction mixture completion.

24. The calcium gluconolactate compound of claim 1, wherein the calcium gluconolactate compound has a structure (I):

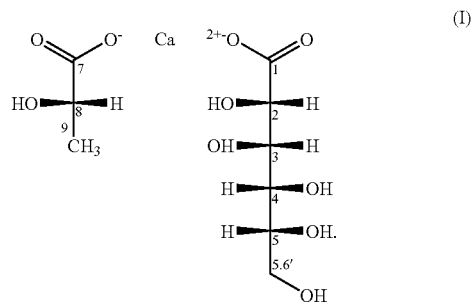

* * * * *